US006565638B1

(12) United States Patent
Sugita et al.

(10) Patent No.: US 6,565,638 B1
(45) Date of Patent: May 20, 2003

(54) PORTABLE AIR-BORNE BACTERIA SAMPLER

(75) Inventors: Naoki Sugita, Tokyo (JP); Yutaka Hatta, Tokyo (JP); Takeshi Yamada, Tokyo (JP); Yukihiro Nakata, Tokyo (JP)

(73) Assignee: Midori Anzen Co., Ltd., Tokyo (JP)

( * ) Notice: Subject to any disclaimer, the term of this patent is extended or adjusted under 35 U.S.C. 154(b) by 0 days.

(21) Appl. No.: 09/807,868

(22) PCT Filed: Oct. 20, 1999

(86) PCT No.: PCT/JP99/05784

§ 371 (c)(1),
(2), (4) Date: Jun. 7, 2001

(87) PCT Pub. No.: WO00/24865

PCT Pub. Date: May 4, 2000

(30) Foreign Application Priority Data

| | | |
|---|---|---|
| Oct. 26, 1998 | (JP) | 10-304067 |
| Oct. 26, 1998 | (JP) | 10-304068 |
| Apr. 19, 1999 | (JP) | 11-110302 |
| Apr. 19, 1999 | (JP) | 11-110303 |

(51) Int. Cl.[7] .......... G01N 1/00

(52) U.S. Cl. .......... 96/413; 73/28.05; 73/863.22

(58) Field of Search .......... 96/413; 55/320, 55/418; 73/28.05, 863.21, 863.22

(56) References Cited

U.S. PATENT DOCUMENTS

| | | | | |
|---|---|---|---|---|
| 3,922,905 | A | * 12/1975 | Roth | 73/28.04 |
| 6,094,997 | A | * 8/2000 | Lemonnier | 73/863.22 |
| 6,294,375 | B1 | * 9/2001 | Chevalier | 435/287.1 |
| 6,342,388 | B1 | * 1/2002 | Van Den Wildenberg | 435/287.1 |

FOREIGN PATENT DOCUMENTS

| | | |
|---|---|---|
| JP | 5-68300 | 9/1993 |

* cited by examiner

*Primary Examiner*—Robert A. Hopkins
(74) *Attorney, Agent, or Firm*—Varndell & Varndell, PLLC

(57) ABSTRACT

After supporting a petri dish S having a culture medium K contained therein with a given thickness on a petri dish holder 17 of a housing 14, a nozzle holder 13 is clamped at a top of the housing 14. When a motor 19 is energized to rotate a high static pressure fan 18, air is introduced through nozzle openings 12*a*, and flows through a space between the nozzle 15 and the culture medium K. By setting a distance between the nozzle and the culture medium to 0.5–1.5 mm, a high collection efficiency can be attained.

8 Claims, 9 Drawing Sheets

Air-flow velocity vs Collection Efficiency

Collection Efficiency for Bacillus Subtilis %

Air-flow velocity through Nozzle [m/s]

PORTABLE AIR-BORNE BACTERIA SAMPLER

CROSS-REFERENCE TO RELATED APPLICATIONS

This application is a U.S. national phase application of International Application No. PCT/JP99/05784 filed Oct. 20, 1999, which application was not published in English.

TECHNICAL FIELD

The present invention relates to a portable type airborne microorganism sampler for collecting airborne microorganisms in a room for monitoring and managing a pollution due to microorganisms and bacteria and fungi.

TECHNICAL BACKGROUND

There have been proposed a stationary type airborne microorganism sampler and a portable type airborne microorganism sampler for monitoring a condition of microorganism pollution by collecting airborne microorganisms such as bacteria and fungi in pharmaceutical factories and food factories and public spaces such hospitals.

Particularly, a portable type light weight airborne microorganism sampler has been used for managing and checking a pollution within a space where a condition of microorganism pollution has to be monitored and managed such as biological clean room and manufacturing lines in the pharmaceutical factories and food factories.

Figure 11:
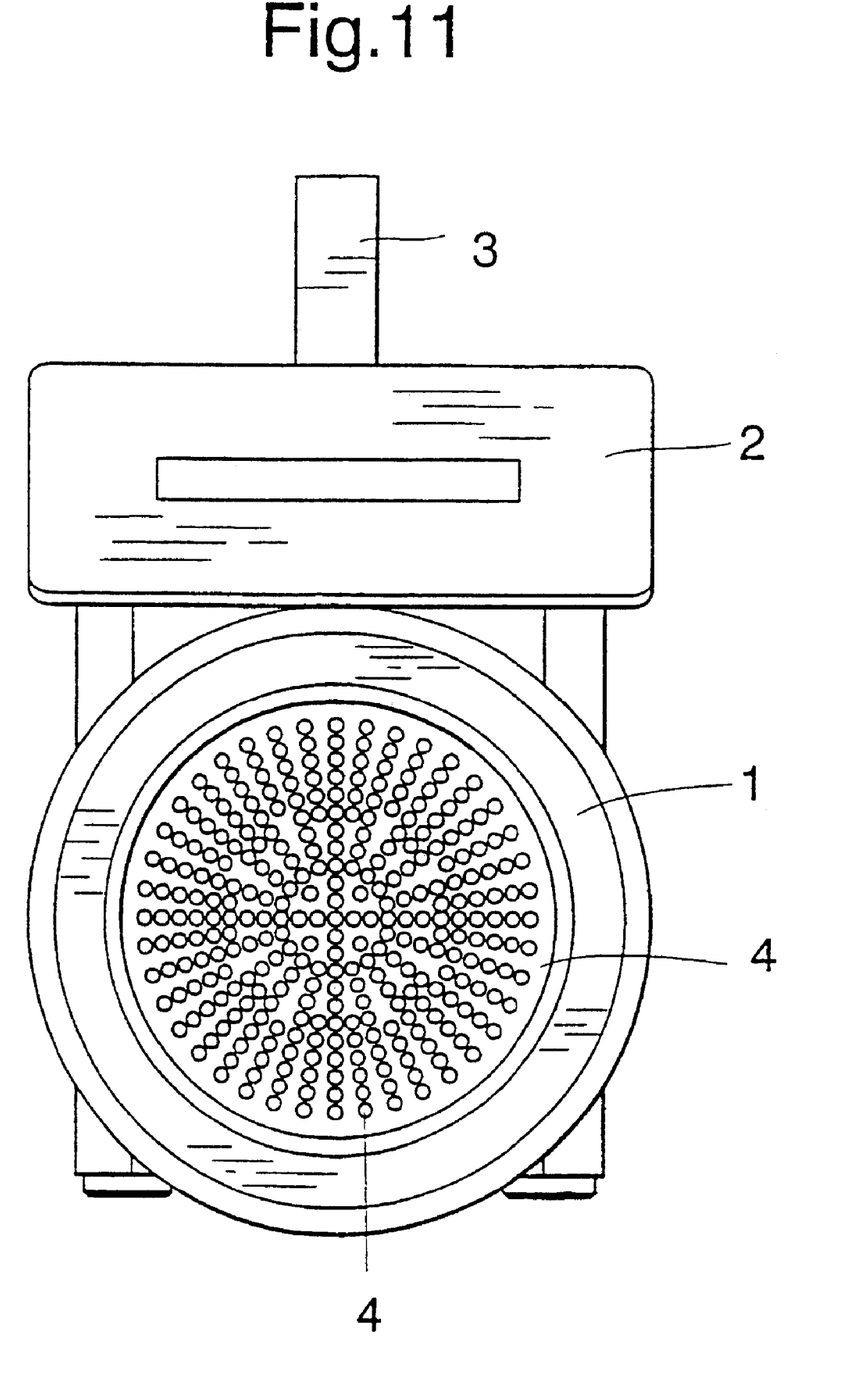
FIG. 11 is a plan view showing a known sampler.

FIG. 11 is a plan view showing a known portable type sampler, which is mainly consisting of a collecting section 1 and an operating section 2. The operating section 2 has a handle 3 by means of which a user can carry the sampler. At a front end of the collection section 1, there is clamped a nozzle portion 4 through which an air is introduced for collecting airborne microorganisms. The nozzle portion 4 has a number of openings 5 arranged radially.

(1) In the known air sampler mentioned above, the stationary type sampler has a sufficiently high collection efficiency, measured by JIS method, because the measurement is carried out under the JIS method, but it uses a large suction pump, and therefore it is liable to be large in size and heavy in weight. Moreover, AC 100V power supply is required as the main power, and therefore it is difficult to conduct the measurement at any place.

Although the portable type air sampler can be small in size and light in weight by using a small fan such as sirocco fan and radial fan, a high static pressure could not be attained. Therefore, in order to introduce a sufficiently large air-flow rate through the nozzle portion 4, the nozzle openings have to be configured such that the sampler can operate under a low static pressure, but this makes a collection efficiency low. If the suction nozzle is configured to have a high collection efficiency, a sufficiently large air-flow rate could not be realized by a static pressure of about 200 Pa which is obtained by the radial fan. Then, air-flow velocity through the nozzle portion 4 becomes lower and a high collection efficiency could not be attained.

(2) Furthermore, in the portable type airborne microorganism sampler, use is made of a fan motor for generating an air flow for collecting microorganisms, carbon particles are produced by a brush portion of the motor and further droplets of a lubricant oil are generated. In the known airborne microorganism sampler, these particles and droplets are spread out of an exhaust port of the sample together with an air flow and might contaminate a clean room.

(3) Moreover, since the nozzle openings 5 are arranged radially, the number of nozzle openings per unit surface area of the nozzle portion 4 varies depending upon positions thereof. This results in that a quantity of an air flow passing through the nozzle portion per unit surface area thereof varies. In a place where a larger air-flow rates, the culture medium is liable to be dried to decrease a collection efficiency and even after the incubation, a colony is hardly formed. In a place where a distance between successive nozzle openings 5 is small, since collected microorganisms come closer to each other and colonies might be contacted with each other, and then the number of colonies could not be counted accurately.

The present invention has for its object to provide a small and light portable type airborne microorganism sampler, which can solve the above mentioned problem (1), and has a high collection efficiency.

It is another object of the invention to provide a small and light portable type airborne microorganism sampler, which can solve the above problem (2) and can collect airborne microorganisms positively without contaminating a surrounding environment.

It is another object of the invention to provide a portable type airborne sampler, which can solve the above mentioned problem (3), can produce a uniform air flow through a nozzle portion per unit surface area thereof, and can measure precisely the number and positions of colonies produced after collection and cultivation.

DISCLOSURE OF THE INVENTION

According to the invention, a portable type airborne microorganism sampler comprises a nozzle having a plurality of openings formed therein, a nozzle holder supporting said nozzle, a petri dish holder arranged at a downstream position of an air flow supporting a petri dish containing a culture medium, and a fan generating the air flow, characterized in that a distance between a surface of the culture medium and said nozzle is set to 0.5–1.5 mm.

According to further aspect of the invention, a portable type airborne microorganism sampler comprises a nozzle having a plurality of openings formed therein, a nozzle holder supporting said nozzle, a petri dish holder arranged at a downstream position of an air flow supporting a petri dish containing a culture medium, and a fan generating the air flow, characterized in that an air-flow velocity through the openings of nozzle is set to be not lower than 20 m/sec.

According to further aspect of the invention, a portable type airborne microorganism sampler comprises a nozzle having a plurality of openings formed therein, a nozzle holder supporting said nozzle, a petri dish holder arranged at a downstream position of an air flow supporting a petri dish containing a culture medium, and a fan generating the air flow, characterized in that said openings of nozzle are arranged in a grid-like manner.

BEST MODE OF THE INVENTION

Figure 1:
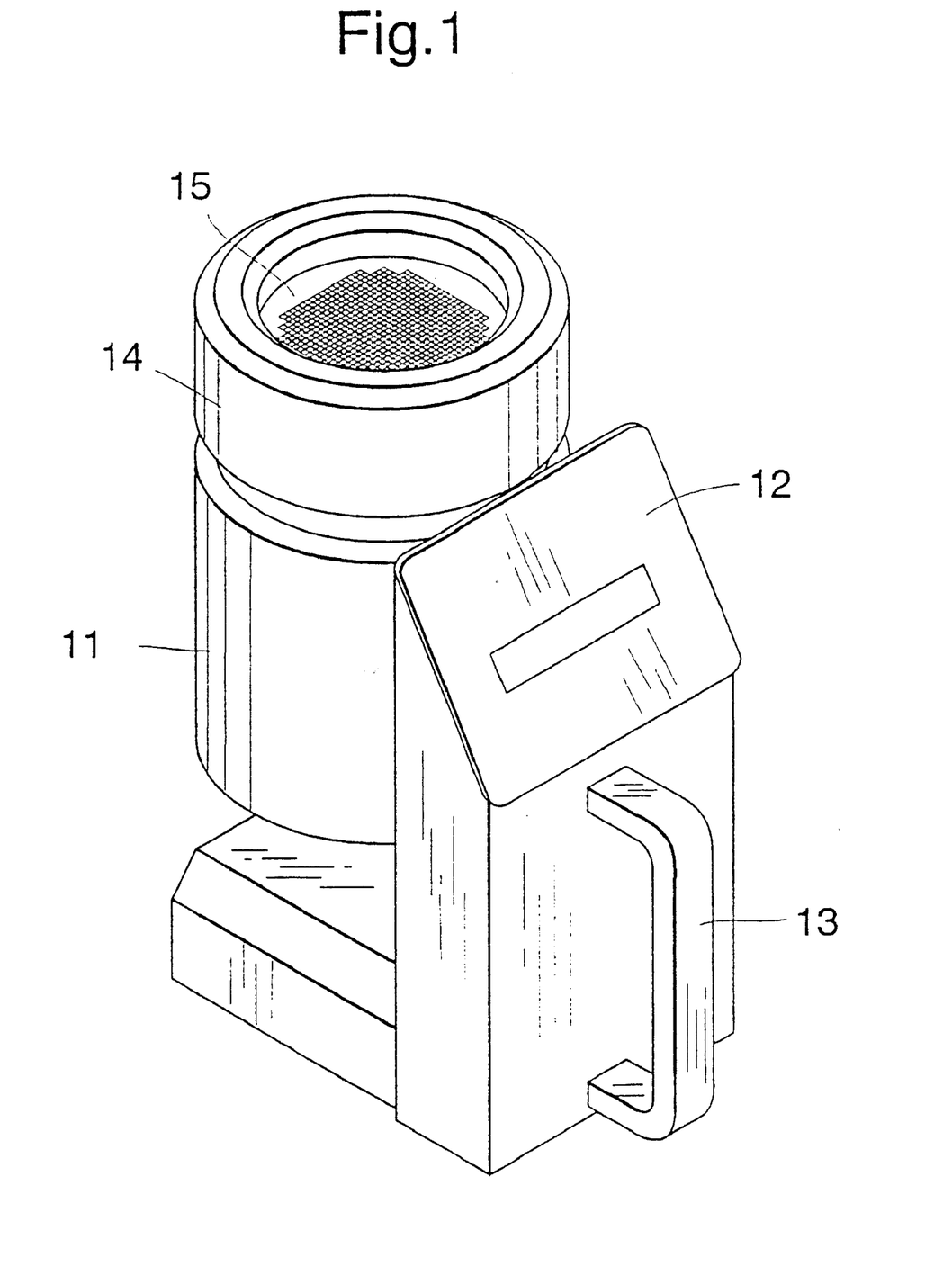
FIG. 1 is a perspective of the sampler.
Figure 2:
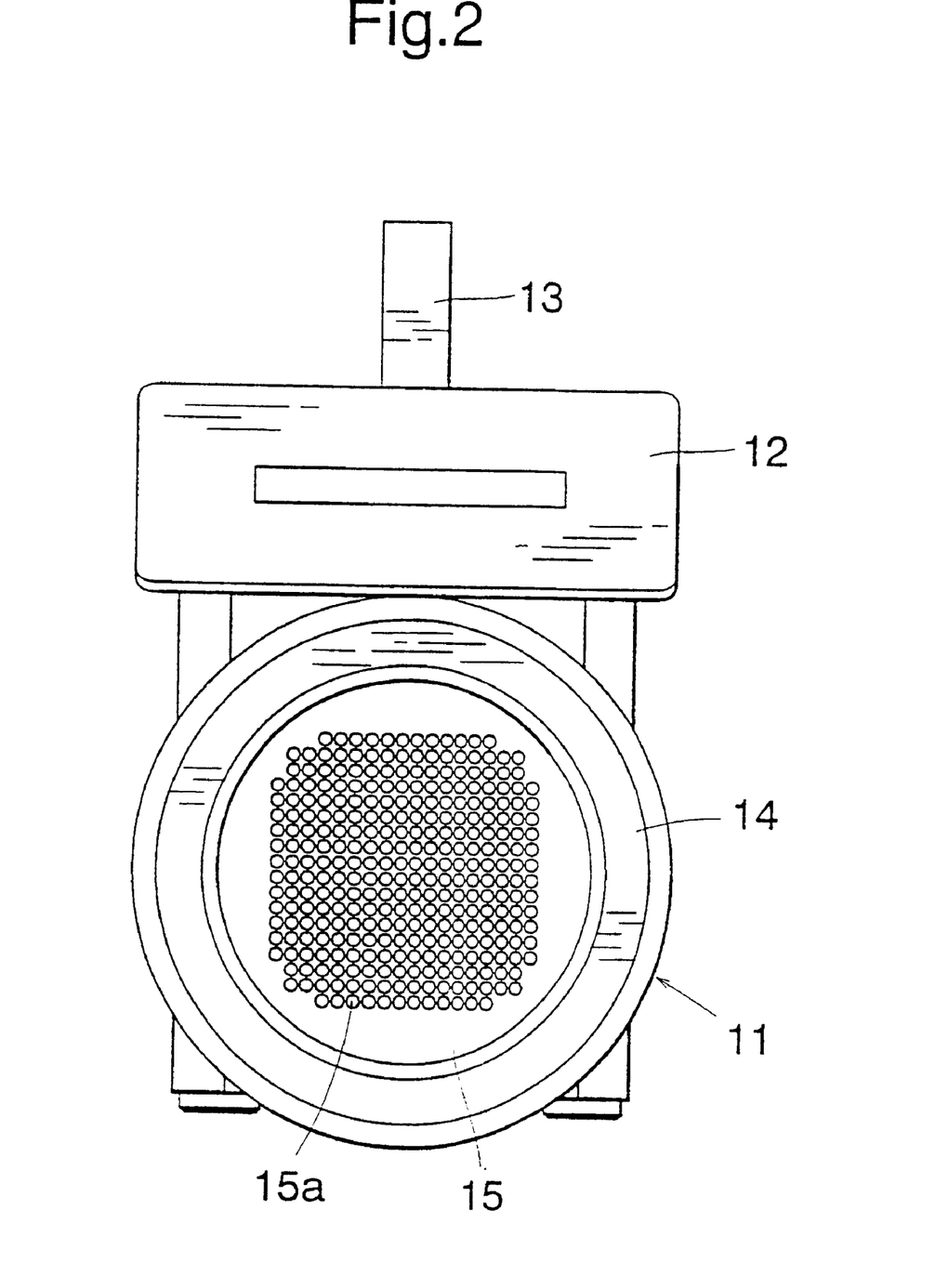
FIG. 2 is a plan view thereof.
Figure 3:
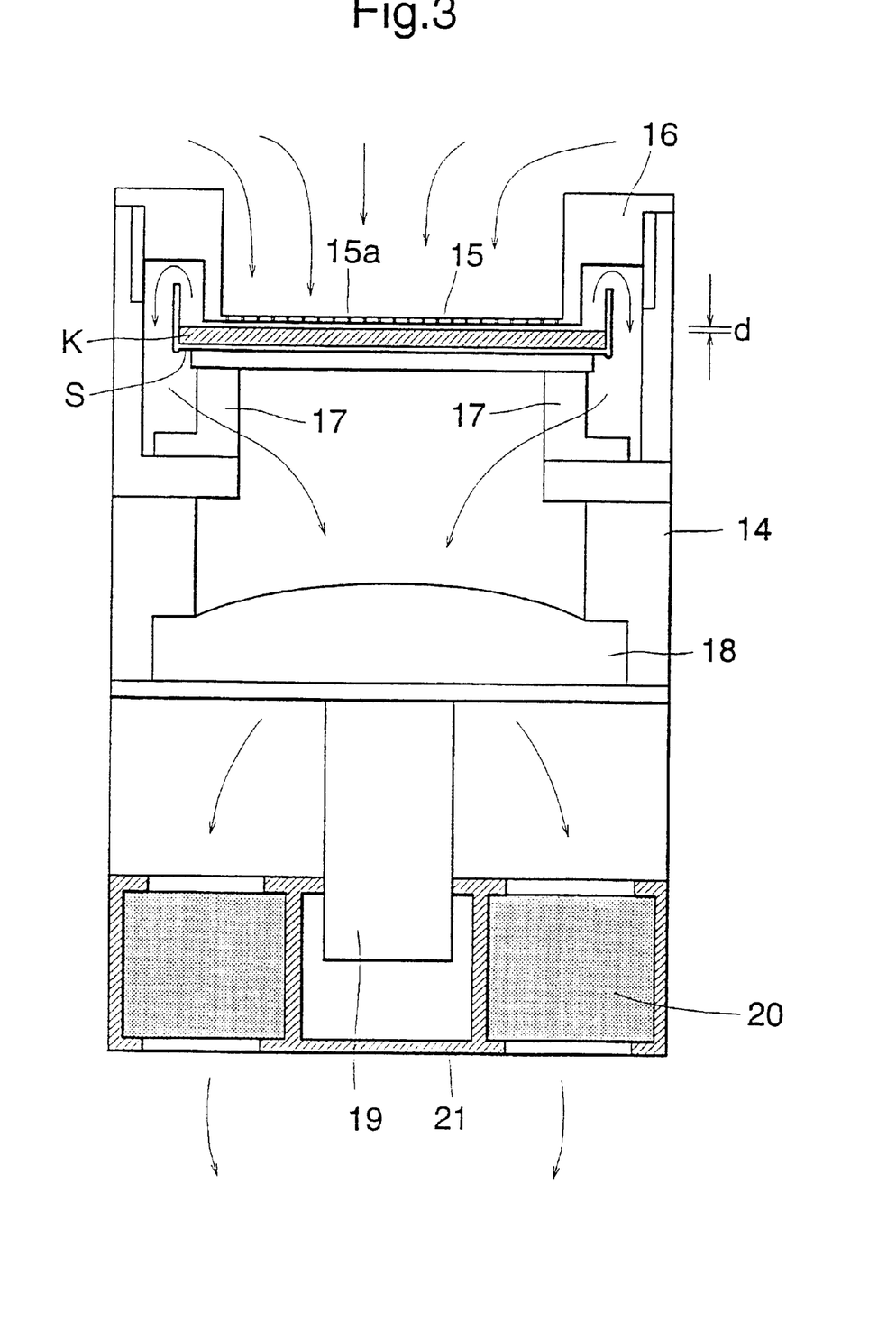
FIG. 3 is a cross sectional view thereof.
Figure 4:
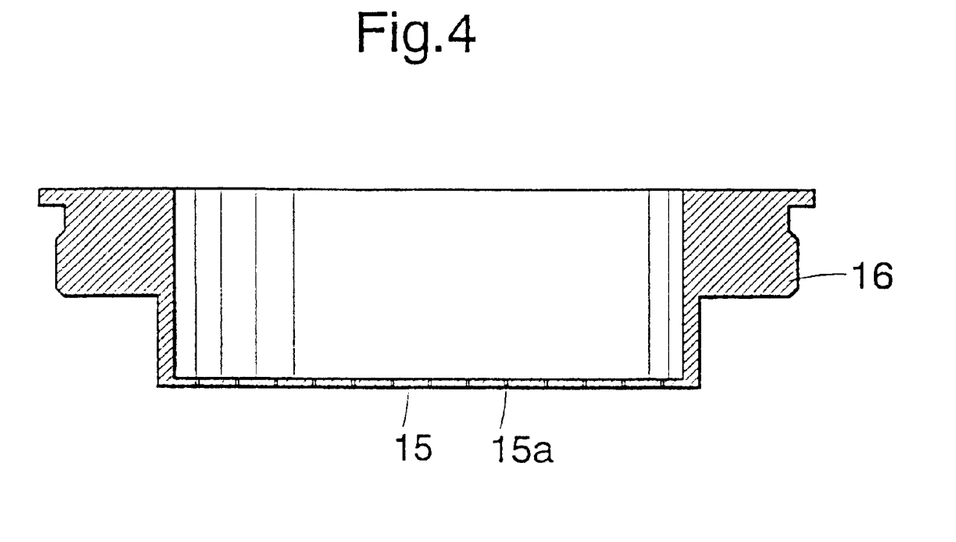
FIG. 4 is a side view of a nozzle.
Figure 5:
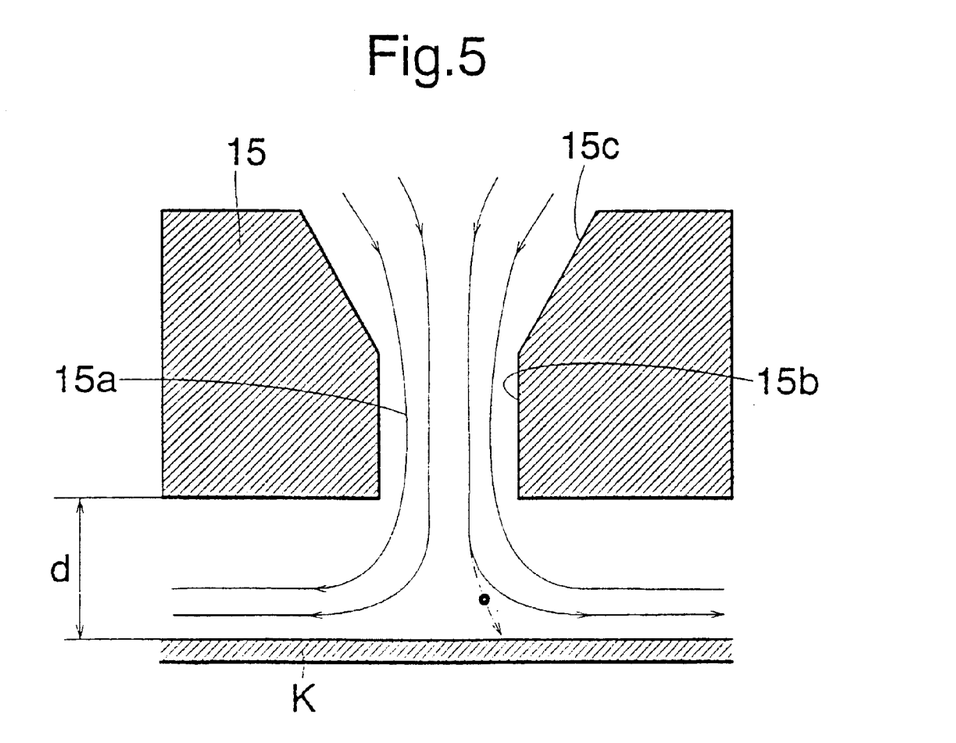
FIG. 5 is a cross sectional view of an opening of the nozzle.

FIG. 1 is a perspective view showing the portable type airborne microorganism sampler according to the invention, FIG. 2 is a plan view thereof, and FIG. 3 is a cross sectional view thereof. The portable type sampler is mainly composed of a collecting section 11 for collecting airborne microorganisms and an operating section 12. The operating section 12 includes a grip 13 for carrying the sampler. The collecting section 11 comprises a cylindrical housing 14 and a nozzle 15 having a number of fine nozzle openings 15a formed therein, said nozzle being supported by a nozzle support 16 at a top of the housing 14 as illustrated in FIG. 4. The nozzle openings 15a are arranged in a grid-like manner, and an opening is formed by a straight tube portion 15b having a diameter of 0.36 mm and a height of 0.5 mm and a tapered portion 15c having a open angle of 90 degrees and a height of 0.5 mm as depicted in FIG. 5, the taped portion serving to reduce a pressure loss in the nozzle 15.

In order to avoid an air leakage, the nozzle holder 16 is screwed to the housing 14. A chalet holder 17 is provided immediately below the nozzle 15, said chalet holder supporting a petri dish S which contains a culture medium K. A distance d between the nozzle 15 and the culture medium K is set to 0.5–1.5 mm. Within a space formed underneath the petri dish holder 17, there are arranged a high static pressure fan 18 such as turbofan and vortex blower, a motor 19 for driving the high static pressure fan 18 and a control circuit, and an air-flow velocity not lower than 20 m/sec can be attained. An exhaust filter 20 is arranged at a lowermost position.

Upon operation, the petri dish S having the culture medium K contained therein with a given thickness is supported by the petri dish holder 17 in the housing 14, and then the nozzle holder 16 is clamped at the top of the housing 14. When the motor 19 is driven to rotate the high static pressure fan 18, an air is introduced through the nozzle openings 15a and flows though a space between the nozzle 15 and the culture medium K as illustrated in FIG. 5. When the air-flow velocity through the nozzle 15 is set to be not lower than 20 m/sec, the culture medium K serves as a collection plate, and airborne microorganisms such as bacteria and fungi are impacted against a surface of the culture medium K by inertia force and are collected thereby. After that, the air stream is sucked by the high static pressure fan 18 through a space formed in a circumferential portion and is exhausted through the exhaust filter 20 as shown by arrows in FIG. 3.

Figure 6:
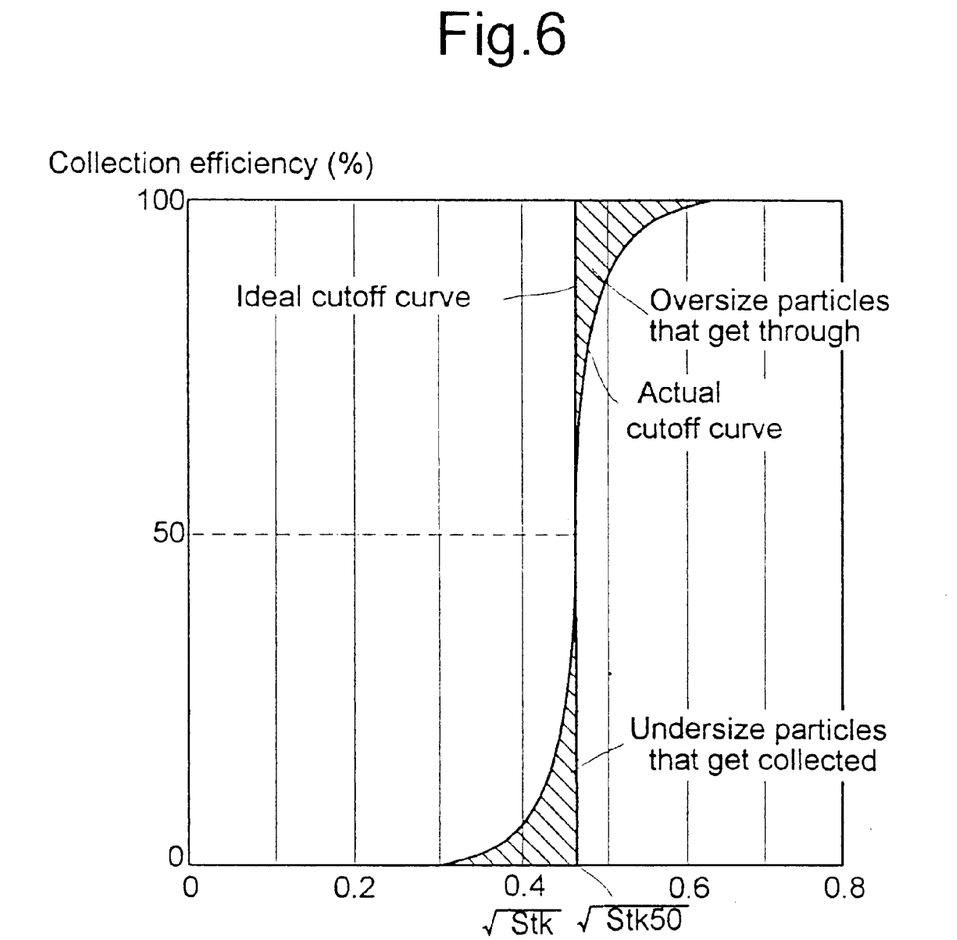
FIG. 6 is an actual and ideal impactor cutoff curves.

Now it is assumed that *bacillus subtilis* having a particle size of 0.7 μm are to be collected effectively. According to an ideal graph representing a relationship between a limit particle size and a collection efficiency shown in FIG. 6 (Aerosol Technology, page 114, FIG. 5.8, "Ideal and Practice of Limit Particle Size of Impact", published on Apr. 10, 1985 from INOUE SHOIN Co. Ltd. Japan), when it is desired to attain a collection efficiency not lower than 50%; a Stokes number $S_{tk}$ is preferably set to be not lower than 0.22 ($S_{tk}^{1/2}$ not lower than 0.47), when it is desired to realize a collection efficiency not lower than 95%, a Stokes number $S_{tk}$ is preferably set to be not lower than 0.3 ($S_{tk}^{1/2}$ not lower than 0.55). It should be noted that the Stokes number $S_{tk}$ may be defined by the following equation, wherein a particle density is ρ, a particle size is d, an air-flow velocity U, Cunningham constant C, an air viscosity η, and a nozzle opening inner diameter D.

$$S_{tk} = \rho d^2 UC / 9\eta D \tag{1}$$

When the known portable type airborne microorganism sampler is experimentally used to collect *bacillus subtilis* having a particle size of 0.7 μm, a collection efficiency of about 10% is obtained under a condition that an air-flow velocity is 11.8 m/sec and a nozzle opening diameter is 0.6 mm. From the equation (1), this corresponds to a case in which a stokes number $S_{tk}$ is about 0.07 ($S_{tk}^{1/2}$ is about 0.27), and a sufficient collection could not be carried out. In order to increase a collection efficiency not less than 90% for *bacillus subtilis*, it is necessary to increase the Stokes number $S_{tk}$ to 0.2–0.3 ($S_{tk}^{1/2}$=0.45–0.55). In order to attain $S_{tk}=0.3$, from the equation (1), an air-flow velocity should be increased to 48.4 m/sec which is higher than the known value by about 4.1 times.

However, it has been generally known that a pressure loss is increased in proportion to a square of an air-flow velocity, and therefore since both pressure loss and an air-flow rate are increased, a necessary workload is increased by 69 times. Therefore, such a system could not be realized practically.

As expressed by the equation (1), the Stokes number $S_{tk}$ in inversely proportional to an inner diameter of a nozzle opening, the smaller a diameter of a nozzle opening is, the larger the Stokes number $S_{tk}$ is obtained, and thus a collection efficiency is increased. Therefore, a diameter of nozzle opening is reduced from 0.6 mm to 0.36 mm, a necessary air-flow velocity for increasing a collection efficiency for *bacillus subtilis* not less than 90% can be reduced. This results in that a pressure loss is decreased and a necessary electric power can be reduced. In order to realize such a high static pressure, it is preferable to use a turbofan having a static pressure not less than 400 Pa under a nominal air-flow velocity.

Figure 7:
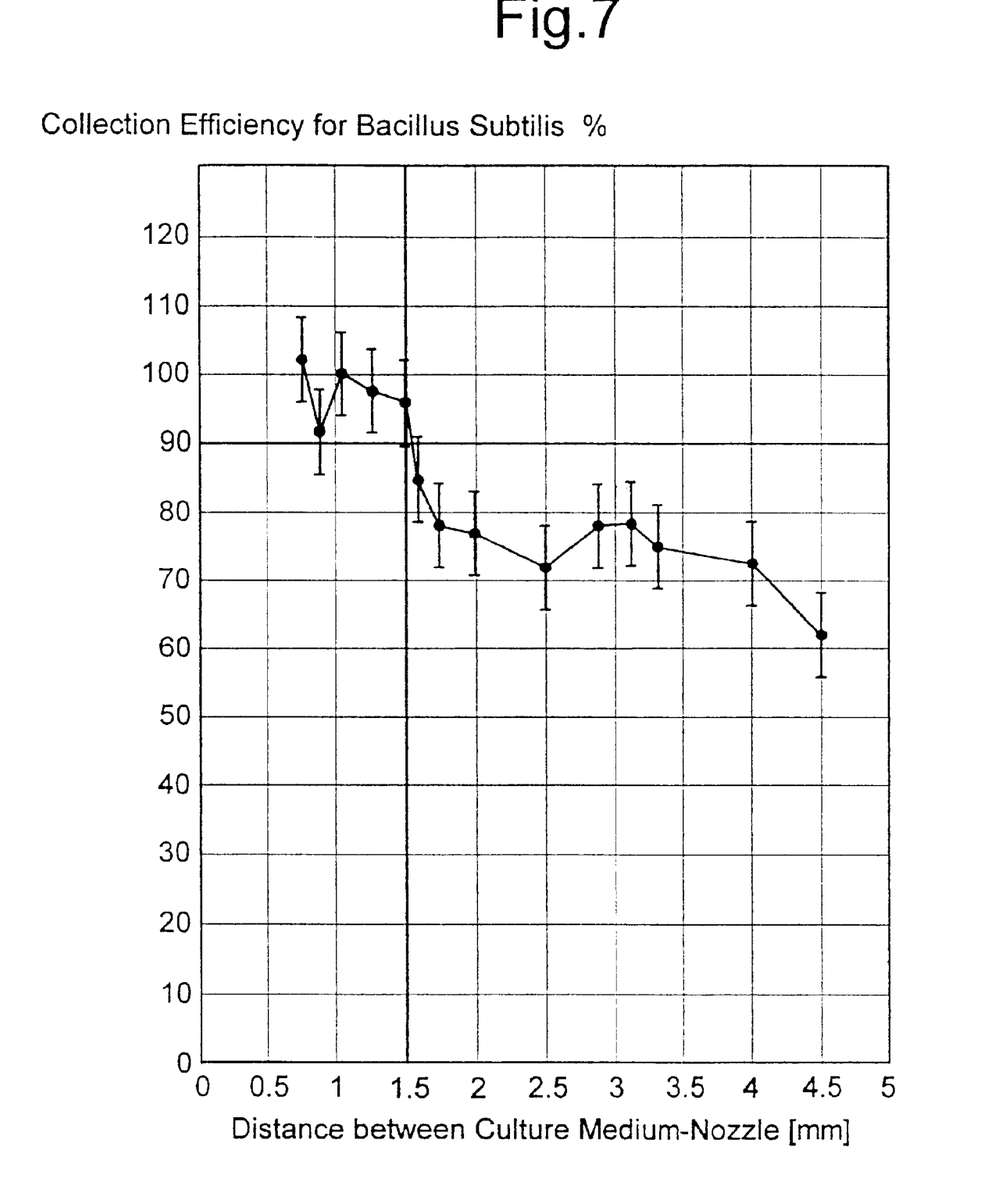
FIG. 7 is a graph representing a relationship between a culture medium-nozzle distance and a collection efficiency.

The inventors have found experimentally that a collection efficiency is affected not only by a Stokes number $S_{tk}$, but also by a distance between the culture medium and the nozzle. A collection efficiency is mainly dependent upon this distance, and when this distance is too short, a quantity of air is increased and a collection efficiency is decreased, and when this distance is too large, a velocity of particulate substances impacting upon the culture medium is decreased and a collection efficiency is also decreased. From experiments, it has been found that when a distance between the culture medium and the nozzle is shorter than 1.5 mm, a collection efficiency becomes not less than 90%, and when the distance is longer than 1.6 mm, a collection efficiency becomes not higher than 85% as shown in FIG. 7.

Therefore, according to the invention, a distance between the culture medium and the nozzle is set to a value within a range of 0.5–1.5 mm. Then, it is possible to attain a higher collection efficiency than the known portable type sampler, and this efficiency is not less than that obtained by the known stationary type sampler.

From the equation (1), in case of $S_{tk}=0.3$, it is necessary to increase a wind speed higher than the known value by about 4.1 times. However, by decreasing the number of nozzle openings 15a to reduce a quantity of air by 4.1 times, a necessary electric power can be reduced by 4.1 times. Even in such a case, a workload (W) becomes larger than the original value by about 17 times. Since the Stokes number $S_{tk}$ is inversely proportional to a diameter of a nozzle opening, the smaller a diameter of a nozzle opening is, the larger the Stokes number $S_{tk}$ is obtained, and thus a collection efficiency is increased. Therefore, when a diameter of nozzle opening is reduced from 0.6 mm to 0.36 mm, a necessary air-flow velocity for increasing a collection efficiency for *bacillus subtilis* having a particle size of 0.7 $\mu$m not less than 90% can be reduced from 48.4 m/sec to 29.0 m/sec. When an air-flow is decreased, a pressure loss is reduced, and thus a necessary electric power can be decreased.

Figure 8:
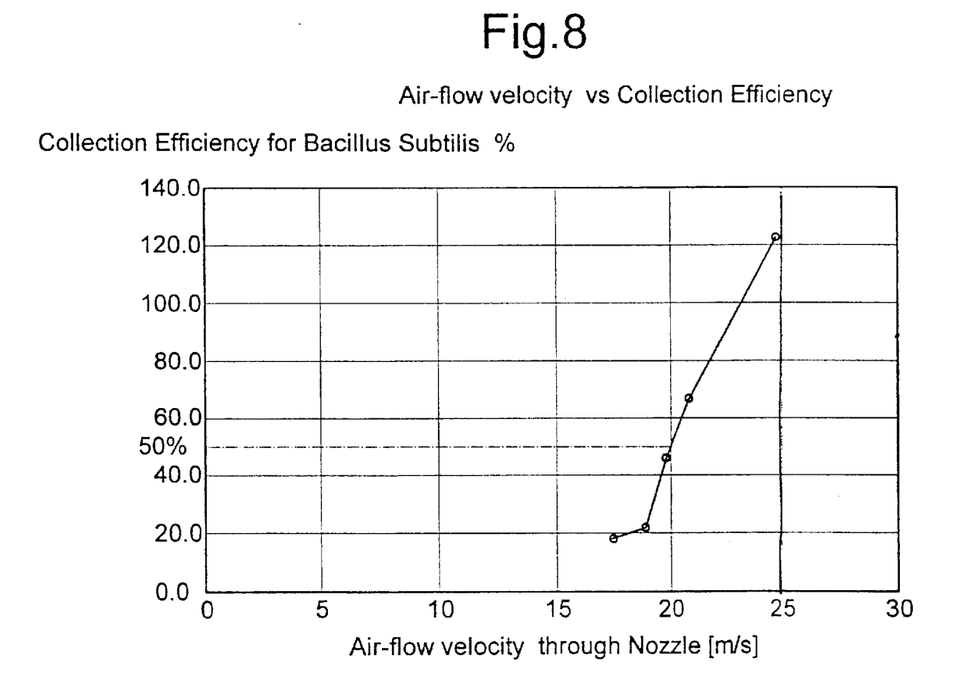
FIG. 8 is a graph denoting a relationship between a air-flow velocity through the nozzle and a collection efficiency.

In the present embodiment, a relationship between an air-flow velocity of an air stream passing through the nozzle portion and a collection efficiency is experimentally represented by a graph shown in FIG. 8. From this result, it is understood that in order to obtain a collection efficiency not lower than 90%, an air-flow velocity of about 23 m/sec is required, and a minimum collection efficiency not lower than 50% is realized by an air-flow velocity not lower than 20 m/sec.

In practice, a collection efficiency not lower than 50% is very effective, but in the known portable type sampler, since use is made of a radial fan, a high static pressure is not obtained and a sufficiently high collection efficiency could not be attained.

Therefore, in the present embodiment, in order to realize an air-flow velocity not lower than 20 m/sec, use is made of a turbofan having a static pressure not lower than 400 Pa under a nominal air-flow rate to solve the problem of low static pressure, and a higher collection efficiency than the known portable type sampler can be obtained. The portable type sampler according to the invention has a comparative performance to the known stationary type sampler.

Usually the sampler is used within a clean room, and thus it is necessary to make an exhausted air from the sampler to be clean substantially equal to or much cleaner than an atmosphere in the clean room. To this end, the filter 20 for purifying the exhausted air is provided at a downstream position with respect to the fan motor 19 near the exhaust port. The filter 20 has a highly purifying capability and may be preferably formed by a HEPA (High Efficiency Particulate Air) filter made of glass fibers, which can collect particles having a size of 0.3 $\mu$m by not lower than 99.97%. If a further purification is required in order to reduce the number of particles exhausted from the sampler, it is preferable to use a ULPA (Ultra Low Penetration Air) filter which is made of a glass and has a collection efficiency not lower than 99.999% for particles having a size of 0.1–0.2 $\mu$m.

The filter 20 is formed by folding a filter sheet by a mini-pleat treatment with a folded width not wider than 75 mm. In the portable type sampler according to the invention, in order to loose an advantage of small size and light weight, it is preferable to reduce a thickness of the filter 20. Then, a pleat folding width is preferably set to 15–50 mm, and in a practical sampler, a pleat folding width is set to 25 mm. By using such a filter 20, a high collection efficiency and low pressure loss can be maintained.

Dust particles or debris might leak from a space between the filter 20 and the housing, and therefore it is necessary to provide a sufficient sealing around the filter, but in order to save a space, the filter 20 is formed to have a central hole into which a part of the motor 19 is projected. In this case, a filter supporting and sealing frame 21 is detachably secured to the sampler main body in order to prevent a leakage of the air stream at a downstream position of the motor as shown in FIG. 3.

Figure 9:
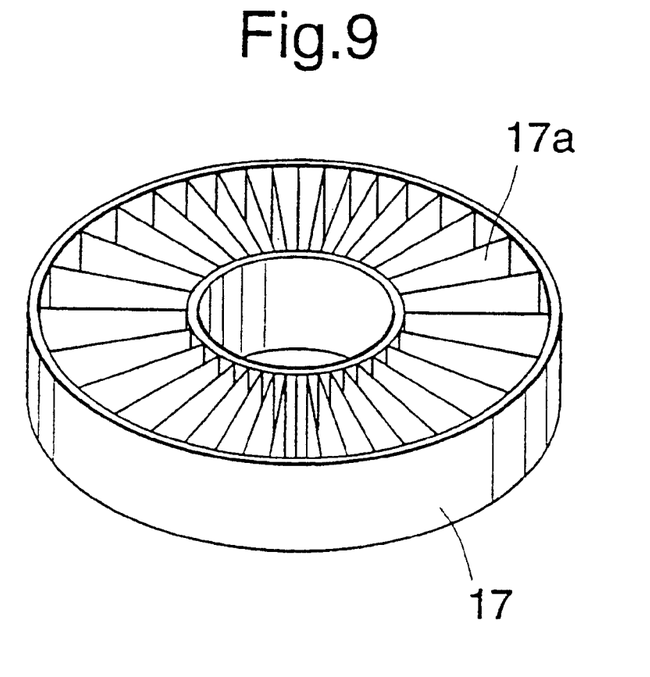
FIG. 9 is a perspective view showing a radially pleated filter.
Figure 10:
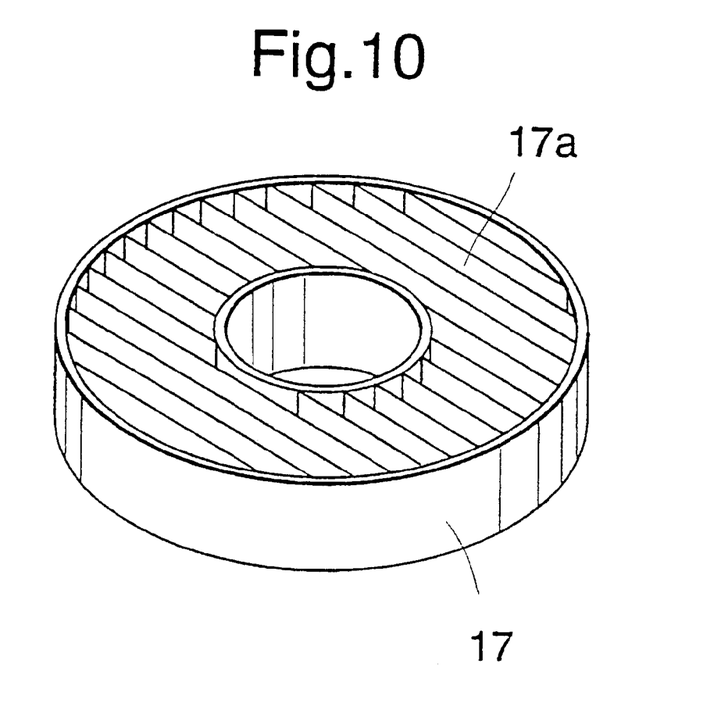
FIG. 10 is a perspective view illustrating a parallelly pleated filter.

The filter 20 having the pleated portion as well as the above mentioned central hole may preferably be formed in a circular shape by pleating the filtering member 17a as shown in FIG. 9 or in a circular shape by pleating the filtering member parallelly as shown in FIG. 10, because the sampler main body has a tubular shape for installing the circular petri dish.

In the radially pleated filter, a distance between successive ridges in an inner area becomes different from a distance between successive ridges in an outer area, and thus there is produced a small unevenness in a pressure loss. The parallelly pleated filter is superior to the radially pleated filter in this point. On the other hand, the radially pleated filter can be manufactured much more easily than the parallelly pleated filter. Therefore, either one may be selected suitably by also considering the existence of the central hole for escaping the motor.

In general, the portable type sampler is used under such a condition that the electric power supply is limited. That is to say, the portable type sampler is energized with a dry battery or rechargeable battery. Therefore, the filter 20 might increase in a pressure loss and a load of the motor 19 is increased. Then, a power consumption (an air-flow velocity×a total sum of pressure losses×a coefficient) might be increased. Therefore, a usable time period is shortened and an operation time is reduced. In order to obtain a same operation time, it is necessary to provide a battery of a large capacity. Then, the sampler becomes large in size and heavy in weight and the merits of the portable type might be lost.

Accordingly, it is preferable that when the high static pressure fan 18 having a static pressure under a nominal air-flow rate is used under an air-flow velocity of not lower than 20 m/sec passing through the nozzle openings, the filter 20 is constructed such that a static pressure becomes not higher than 10%, more preferably 8% of the static pressure of the high static pressure fan 18 under a nominal quantity of the air flow. In the present embodiment, the filter is set such that the static pressure becomes 100 Pa which is equal to 10% of a static pressure of about 1000 Pa of the high static pressure fan 18 under a nominal quantity of the air flow. Then, an increase in the power consumption can be limited to about 10%. In an actual use, a negligible reduction in an operating time, i.e. measuring period could be attained. In this manner, although the transitivity is reduced by the filter 20, the exhausted air can be purified sufficiently without decreasing an operation time.

In the present embodiment, the nozzle openings 15a are aligned regularly with a pitch of 2.6 mm along the up and down direction as well as along the right and left direction, i.e. in a square grid-like manner. Therefore, after incubation, colonies are also formed regularly along the nozzle openings 15a, and the colonies can be counted easily without fail without using a special method or special colony counting device. Then, the colony counting can be easily carried out by inexperienced persons with a substantially same level as experienced persons.

The number of the nozzle openings 15a is preferably set such that a total surface area of the nozzle openings is not smaller than 28.3 mm$^2$. This total surface area of 28.3 mm$^2$ of the nozzle openings may be calculated from an air-flow rate passing through the nozzle 15 per unit time such that an air-flow velocity at the nozzle 15 becomes 20 m/sec can be obtained.

Since the nozzle 15 has the openings 15a such that a total surface area of the openings is 28.3 mm$^2$, an air-flow velocity passing through the nozzle 15 becomes not lower than 20 m/sec, and the culture medium K effectively serves as a collection plate, and microorganisms such as bacteria and fungi can be impacted by inertia force upon the surface of the culture medium K and can be collected effectively.

When the nozzle openings are arranged radially like as the known sampler shown in FIG. 11, the number of nozzle openings varies depending upon positions on the nozzle 15, and the number of nozzle openings per unit surface area varies. Therefore, an air-flow rate passing through unit surface area of the nozzle differs for respective positions of the nozzle. Then, an air-flow rate projected onto the culture medium K becomes non-uniform and the culture medium might be dried locally and a collection efficiency is liable to be lower at a dried area and a colony is hardly produced even if microorganisms are collected thereon.

In the present embodiment, by arranging the nozzle openings 15a regularly in a square grid-like manner, a quantity of wind per unit surface area of the nozzle 15 can be uniform over the whole surface, and thus the air is projected uniformly up to the surface of the culture medium K in the petri dish S. In this manner, the above problem can be solved.

Furthermore, in order to check or judge collected microorganisms, colonies are formed by culturing the collected microorganisms for more than 24 hours. The inventors have found that a size of colonies is not larger than about 2.5 mm, and therefore the colonies can be formed separately from each other and can be counted when a pitch of the nozzle openings 15a is set not less than 2.6 mm. Moreover, in the known radially arranged nozzle, it is impossible to define a nozzle opening through which a microorganism has passed, and thus it could not be judged whether a colony is not formed even if a microorganism has been collected or because microorganism is shielded by the nozzle. However, in the present embodiment, since the nozzle openings 15a are arranged in a square grid-like manner, a position can be easily determined and the calculation can be performed smoothly.

APPLICABILITY IN THE INDUSTRIAL FIELD

As explained above, in the portable type airborne microorganism collecting sampler according to the invention, by setting a distance between the nozzle and the surface of the culture medium to 0.5–1.5 mm, although the sampler is a small and light portable type one, the sampler can be used with a high collection efficiency for a long time, and can be cheap and can have a high performance.

Furthermore, by setting an air-flow velocity flowing through the nozzle having a plurality of openings formed therein to not less than 20 m/sec, although the sampler is a small and light portable type, the sampler can be used with a high collection efficiency for a long time, can be cheap in price, can be safe and can be easily handled.

Moreover, by arranging a filter at the exhaust port, the exhausted air can be free from dusts and debris, and a contamination of a clean room can be avoided.

Since the nozzle openings of the nozzle for introducing an air for collecting airborne microorganisms are arranged regularly in a grid-like manner, a uniform quantity of air can be projected upon the culture medium in the petri dish, the culture medium can be prevented from being locally dried to decrease a collection efficiency and to form colonies, colonies can be effectively prevented from being contacted with each other after culturing to make the colony count impossible. Therefore, positions and counts of collected microorganisms can be accurately measured.

What is claimed is:

1. A portable type airborne microorganism sampler comprising a nozzle having a plurality of openings formed therein, a nozzle holder supporting the nozzle, a petri dish holder arranged at a downstream position of an air flow supporting a petri dish containing a culture medium, and a fan generating the air flow, a distance between a surface of the culture medium and the nozzle is set to 0.5–1.5 mm, an air-flow velocity of the air flow through the openings of the nozzle being set to be not lower than 20 m/ sec.

2. A portable type airborne microorganism sampler according to claim 1, wherein said fan is a high static pressure fan having a static pressure not lower than 400 Pa under a nominal air-flow rate.

3. A portable type airborne microorganism sampler comprising a nozzle having a plurality of openings formed therein, a nozzle holder supporting the nozzle, a petri dish holder being arranged at a downstream position of an air flow supporting a petri dish containing a culture medium, a fan generating the air flow, a distance between a surface of the culture medium and the nozzle being set to 0.5–1.5 mm, an air-flow velocity of the air flow through the openings of the nozzle being set to be not lower than 20 m/sec, and a filter is arranged at an exhaust port of the air flow.

4. A portable type airborne microorganism sampler according to claim 3, wherein said filter is formed by folding a sheet-like filter member into a pleated form.

5. A portable type airborne microorganism sampler according to claim 4, wherein the filter is formed in a circular shape.

6. A portable type airborne microorganism sampler comprising a nozzle having a plurality of openings formed therein, a nozzle holder supporting said nozzle, a petri dish holder arranged at a downstream position of an air flow supporting a petri dish containing a culture medium, and a fan generating the air flow, characterized in that said openings of nozzle are arranged in a grid-like manner.

7. A portable type airborne microorganism collecting sampler according to claim 6, wherein said nozzle openings are arranged with a pitch not smaller than 2.6 mm.

8. A portable type airborne microorganism collecting sampler according to claim 6, wherein a total surface area of said nozzle openings is set not smaller than 28.3 $mm^2$.

* * * * *